Figure 1:
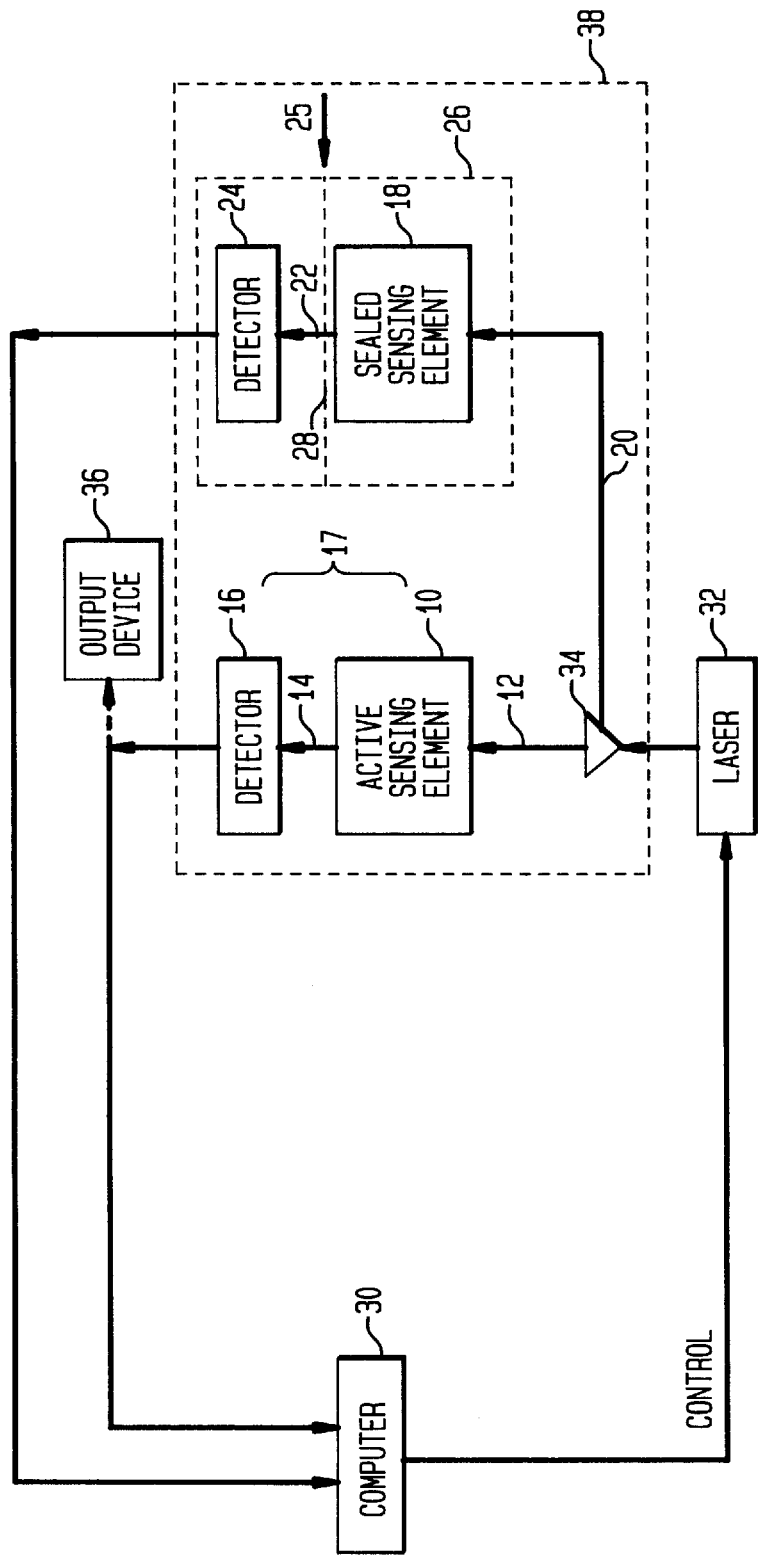

United States Patent [19]
Daniels

[11] Patent Number: 5,835,229
[45] Date of Patent: Nov. 10, 1998

[54] COMPENSATED OPTO-ELECTRONIC SYSTEM AND METHOD FOR GAS SENSING

[75] Inventor: Stuart F. Daniels, Moorestown, N.J.

[73] Assignee: Siemens Corporate Research, Inc., Princeton, N.J.

[21] Appl. No.: 827,148

[22] Filed: Mar. 27, 1997

[51] Int. Cl.$^6$ .................................................. G01N 21/31
[52] U.S. Cl. .......................................... 356/435; 356/437
[58] Field of Search ..................................... 356/435, 437

[56] References Cited

U.S. PATENT DOCUMENTS

| | | | |
|---|---|---|---|
| 5,107,316 | 4/1992 | Jelley et al. | 357/25 |
| 5,191,784 | 3/1993 | Jelley et al. | 73/31.06 |
| 5,317,897 | 6/1994 | Jelley et al. | 73/31.06 |
| 5,572,031 | 11/1996 | Cooper et al. | 356/437 X |

OTHER PUBLICATIONS

"A Dual Mechanism Solid–State Carbon–Monoxide and Hydrogen Sensor Utilizing an Ultrathin Layer of Palladium", Jelley et al., IEEE Transactions on Electron Devices, vol. ED–34, No. 10, Oct. 1987, pp. 2086–2097.

*Primary Examiner*—Vincent P. McGraw
*Attorney, Agent, or Firm*—Adel A. Ahmed

[57] ABSTRACT

A compensated opto-electronic gas sensor system comprises active apparatus utilizing electromagnetic radiation for sensing gas and sealed apparatus utilizing electromagnetic radiation for sensing gas. The sealed apparatus exhibits matched characteristics to the active apparatus and exhibits a sensing sensitivity dependent upon the wavelength of the electromagnetic radiation. The system further includes tunable wavelength source respectively coupled to the apparatus for sensing gas for supplying it with electromagnetic radiation of a selectable wavelength. A computer coupled to at least the sealed apparatus for sensing gas and is responsive to an output thereof for controlling the wavelength of the electromagnetic radiation such that the sealed apparatus for sensing gas exhibits an optimal sensitivity.

25 Claims, 2 Drawing Sheets

COMPENSATED OPTO-ELECTRONIC SYSTEM AND METHOD FOR GAS SENSING

The present invention relates to gas sensor systems and, more particularly, to gas sensor systems including semiconductor sensors for sensing the presence of particular gases in the ambient atmosphere, such as hydrogen component gas.

Sensors are known for detecting and signalling the presence of a gas by the effect of the gas on a semiconductor device. For example, a palladium-gate (Pd-gate) metal-oxide-semiconductor (MOS) structure sensitive to hydrogen gas is known. Such devices include a gate made of a transition metal, typically palladium in place of the conventional gate material generally utilized for an MOS device gate, such as aluminum or polysilicon. In a gas sensing device, the role of such a palladium gate structure is twofold.

First, the gate acts as an electrode in contacting the device, and second, when exposed to hydrogen gas ($H_2$), the palladium gate surface acts as a catalyst in the dissociation of molecular hydrogen into atomic hydrogen, which is then adsorbed on the Pd surface. Some of the atomic hydrogen will diffuse through the bulk palladium and the silicon dioxide ($SiO_2$), layer which typically is deposited under the gate electrode. The adsorbed hydrogen both at the surface and at the interface is polarized and forms a dipole layer. The dipole layer at the interface causes a shift in the threshold voltage ($V_T$) of the MOS structure. The magnitude of the threshold shift due to the dipole layer is approximately proportional to the density of dipoles at the interface, which in turn is related to the concentration of hydrogen in the gas. It is also believed that a change in bulk hydrogen concentration also causes a shift in the work function, which will shift the threshold voltage.

Other gases such as hydrogen sulfide and ammonia have been sensed with a Pd-gate MOS structure. Gases such as carbon monoxide are adsorbed on the palladium surface but are too large molecularly to diffuse through the palladium bulk and therefore, give no response. Response to carbon monoxide has been obtained using a modified Pd gate in which holes from 1.5 to 3.0 $\mu$m in diameter have been patterned through the palladium to permit the carbon monoxide to reach the palladium-silicon dioxide interface.

In a further development, an ultra-thin palladium film has been deposited as an array of small individual islands separated from each other by a distance on the order of a few Å to about 100 Å. The thickness of the film is kept below the point at which the islands tend to merge and, typically, may be in the order of 25 Å. Electrical contact between the individual island globules occurs as a result of electron tunnelling. An account of the foregoing technology is provided, for example, in the article "A Dual Mechanism Solid-State Carbon-Monoxide and Hydrogen Sensor Utilizing an Ultrathin Layer of Palladium" by Kevin W. Jelley and G. Jordan Maclay, IEEE Transactions on Electronic Devices, Vol. ED-34, No. 10, October, 1987.

Sensing of the shift in threshold voltage of the MOS device is typically performed by conventional electrical circuit arrangements. This requires connections to the MOS device, generally to the source and drain electrodes. The need for supply and sensing connections is a disadvantage, for example, in applications in which a sensor is located such that access has to be provided through gas-tight walls or glass window.

Opto-electronic gas sensors capable of operating without the need for electrical connections or supply have been disclosed in U.S. Pat. Nos. 5,107,316, issued Apr. 21, 1992 to Jelley et al.; U.S. Pat. No. 5,191,784, issued Mar. 9, 1993 to Telley et al.; and U.S. Pat. No. 5,317,897, issued Jun. 7, 1994to Jelley et al. The disclosure of the afore-mentioned patents is hereby incorporated by reference in the present application to the extent not inconsistent with the present invention.

Prior art apparatus disclosed in the aforementioned patents for detecting the presence of a gas in an ambient atmosphere comprises a multiple quantum well structure or superlattice; a thin mesh of a transition metal formed on the multiple quantum well structure; and an arrangement for monitoring transmission of electromagnetic radiation through the mesh and the multiple quantum well structure.

Another prior art apparatus disclosed in the aforementioned patents for detecting gas includes a semiconductor device adapted for operation as a gas sensor comprising a body of a semiconductor material including a substrate region and including a multiple quantum well region over the substrate region. The superlattice region has first and second different materials arranged alternately in a plurality of parallel planar layers. The planar layers exhibit an absorption edge for electromagnetic radiation at a first wavelength thereof and have a respective predetermined relatively thin thickness dimension of a value wherein an electric field acting perpendicularly to the planar layers causes the absorption edge to shift to a second wavelength of the electromagnetic radiation. A layer of a transition metal is formed over the superlattice region, the layer of transition metal having a relatively thin thickness dimension. The substrate region has at least a portion thereof removed for providing a clear passage for the electromagnetic radiation.

In another prior art apparatus for detecting a gas disclosed in the aforementioned patents, a semiconductor device adapted for operation as a gas sensor comprises a body of semiconductor material including a substrate region and including a superlattice region over the substrate region. The superlattice region has first and second different materials arranged alternately in a plurality of parallel planar layers. The planar layers exhibit an absorption edge for electromagnetic radiation at a first wavelength thereof and have a respective predetermined relatively thin thickness dimension of a value wherein an electric field acting Perpendicularly to the planar layers causes the absorption edge to shift to a second wavelength of the electromagnetic radiation. A layer of a transition metal is formed over the superlattice region, the layer of a transition metal having a relatively thin thickness dimension. Means are included for reflecting back electromagnetic radiation transmitted towards the layer of transition metal through the superlattice region.

It is known that GaAs/AlGaAs quantum wells experience a shift to longer wavelength in their absorption edge when acted upon by a perpendicular electric field.

In operation, light is transmitted through the structure, as described so as to impinge on a detector. A wavelength somewhat longer than 850 nanometers is selected as to be passed by the GaAs well whose absorption edge is at about 850 nanometers. The palladium layer is then exposed to an atmosphere in which hydrogen may be present which it is desired to detect.

As has been earlier mentioned, it is known that when exposed to hydrogen gas ($H_2$), gas, the palladium surface acts as a catalyst in the dissociation of molecular hydrogen into atomic hydrogen, which is then adsorbed on the Pd surface. Some of the atomic hydrogen will diffuse through the interstices in the palladium mesh and be adsorbed at the surface of the topmost layer of the multiple quantum well structure. The adsorbed hydrogen at the surface is polarized and forms a dipole layer. The dipole layer at the surface results in the effect of a bias being applied to the palladium layer, which causes an electric field to act on the multiple quantum well structure. The high level of doping in the substrate will tend to restrict the resulting electric field to the multiple quantum well structure and thus maximize its effect. The electric field then causes the absorption edge to shift to a longer wavelength.

If the transmitted light being monitored is of the correct wavelength, it will now fall within the shifted absorption edge and the detector will register a drop in intensity and thereby indicate the presence of hydrogen. Naturally the greater concentration of hydrogen in the atmosphere to which the device is exposed, the greater the shift, so that the extent to which light is absorbed or transmitted provides a quantitative measure of the concentration of hydrogen in the ambient atmosphere.

Such opto-electronic sensors have distinct advantages in a number of situations over sensors requiring an electrical supply. These include operation in hazardous or potentially explosive atmospheres, such as in vehicle or aircraft fuel tanks, ship holds, and the like. There are advantages also in remote sensing locations where dispensing with electrical connections for sensing and supply leads is desirable. However, while such sensors can tolerate some degree of variation in component parameters, in actual practice, various tolerances may act to limit the accuracy and dependability of operation.

For example, the absorption edge, upon which operation depends, may exhibit variations due to the influence of manufacturing tolerances on material parameters. Variations are also likely to result from ageing of the devices and from changes in the operating temperature. It is herein recognized that while close matching of characteristics between adjacently formed devices is typically achievable in production, there will generally be a spread in the absolute parameter values between devices not so formed.

Typically, as envisioned in the prior art, the laser source used is of a given wavelength that is appropriately selected for the detection of the absorption edge, or transition region, shift in response to gas adsorption. The selection of this wavelength does not take into account the variation in the absorption edge wavelength between different batches of gas sensing devices nor the effects of ageing and temperature that are unrelated to gas presence. While some degree of variation may be tolerated, such variations will tend to have an undesirable effect on proper operation of the gas detector.

It is furthermore herein recognized that variations in the wavelength of the laser source itself will also have undesirable affects on proper operation of the gas detector.

In accordance with an aspect of the invention, a compensated opto-electronic gas sensor system comprises a first opto-electronic as sensor adapted for exposure to a gas to be detected; a second opto-electronic gas sensor, the second opto-electronic gas sensor being sealed against exposure to the gas and exhibiting closely matched characteristics to the first opto-electronic gas sensor; a wavelength tunable apparatus for providing electromagnetic wave energy to the first and second gas sensors for the operation thereof; and computer apparatus coupled at least to the second opto-electronic gas sensor for sensing the respective output thereof and further coupled to the wavelength tunable apparatus for controlling the wavelength of the electromagnetic wave energy.

In accordance with another aspect of the invention, a compensated opto-electronic gas sensor system comprises an active sensing element and a first detector for detecting an output of the active sensing element; a sealed sensing element and a second detector for detecting an output of the sealed sensing element, the sealed sensing element exhibiting characteristics closely matched to those of the active sensing element; the sensing elements comprising opto-electronic sensing elements of the type exhibiting respective quantum well structures having a transition metal layer for gas detection and exhibiting a respective absorption wavelength edge for electromagnetic wave radiation; a tunable wavelength source of electromagnetic wave radiation coupled providing electromagnetic wave radiation of the same wavelength to each of the active sensing element and the sealed sensing element; and computer apparatus coupled to the first and second detectors and to a control input of the tunable wavelength source of electromagnetic wave radiation for controlling the wavelength of the electromagnetic radiation such that the wavelength is in predetermined relationship to the respective absorption wavelength edge of the sealed sensing element.

In accordance with another aspect of the invention, a Compensated opto-electronic gas sensor system comprises active apparatus utilizing electromagnetic radiation for sensing gas; sealed apparatus utilizing electromagnetic radiation for sensing gas, the sealed apparatus exhibiting matched characteristics to the active apparatus, the apparatus for sensing exhibiting a sensing sensitivity dependent upon the wavelength of the electromagnetic radiation. The system further includes tunable wavelength apparatus respectively coupled to the active apparatus for sensing gas and to the sealed apparatus for sensing gas for supplying electromagnetic radiation of a selectable wavelength thereto; and computer apparatus respectively coupled to at least the sealed apparatus for sensing gas and being responsive to an output thereof for controlling the wavelength of the electromagnetic radiation such that the sealed apparatus for sensing gas exhibits an optimal sensitivity.

In accordance with another aspect of the invention, a compensated method for opto-electronically sensing a gas comprises the steps of transmitting electromagnetic radiation of a given wavelength through a first quantum well structure exhibiting a first absorption band edge, having a thin mesh of a transition metal formed thereon, and being exposed to the gas; transmitting electromagnetic radiation of the given wavelength through a second quantum well structure exhibiting a second absorption band edge, having a thin mesh of a transition metal formed thereon and being shielded from the gas, the first and second quantum well structures exhibiting closely matched characteristics; monitoring electromagnetic radiation transmitted through the second quantum well structure; automatically adjusting the given wavelength until it is in predetermined relationship with the second absorption band edge; and monitoring electromagnetic radiation transmitted through the first quantum well structure for detecting the gas.

In accordance with another aspect of the invention, the step of adjusting the given wavelength until it is in predetermined relationship with the second absorption band edge is performed continuously.

In accordance with another aspect of the invention, the step of adjusting the given wavelength until it is in predetermined relationship with the second absorption band edge is performed periodically.

In accordance with an aspect of the invention, the step of adjusting the given wavelength until it is in predetermined relationship with the second absorption band edge includes a step of sweeping the wavelength over a given range while monitoring electromagnetic radiation transmitted through the second quantum well structure so as to determine the second absorption band edge.

Figure 2:
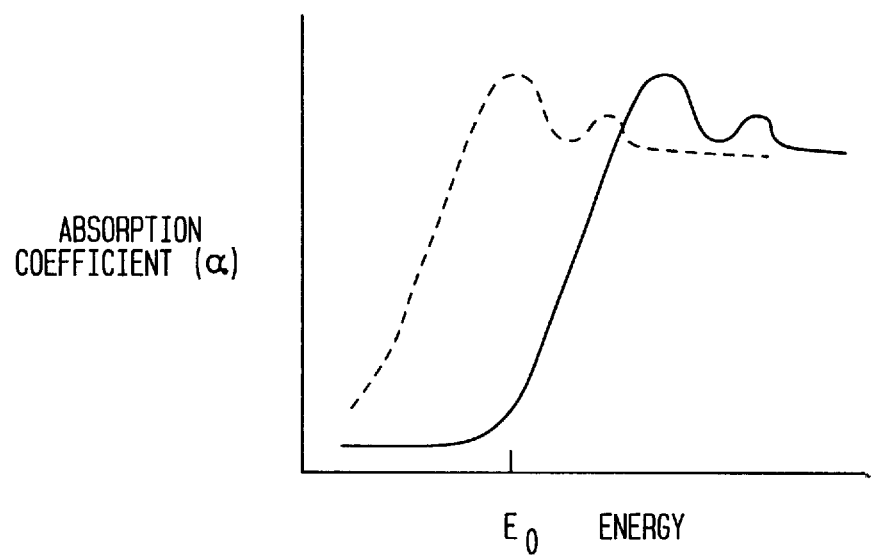

The invention will be better understood from the following detailed description of the best mode known to the applicant in conjunction with the Drawing in which FIG. 1 shows an embodiment in accordance with the principles of the invention; and FIG. 2 shows schematically a characteristic for a device of the type utilized in the invention.

FIG. 1 shows a compensated opto-electronic gas sensor system in accordance with the invention. A first sensing element 10 comprising a quantum well structure having a transition metal layer for gas detection which is essentially similar to the corresponding elements in the prior art arrangements disclosed in the afore-mentioned U.S. Pat. Nos. 5,107,316, 5,191,784, and 5,317,897. A characteristic for such a device is shown schematically in FIG. 2, which is the same as FIG. 2 of the afore-mentioned U.S. Pat. No. 5,191,784. The solid line in the figure indicates the absorption coefficient without the presence of an electric field and the dashed line indicates the absorption coefficient under the action of an electric field such as can occur due to the presence of a gas.

Electromagnetic radiation, such as an infrared beam 12 is transmitted through sensing element 10 and the resulting transmitted beam 14 is applied to a first detector 16 which is essentially similar to the corresponding elements in the prior art arrangements disclosed in the afore-mentioned United States Patents. Sensing element 10 and detector 16 are designated together as an active sensor 17.

A second sensing element 18, comprising a quantum well structure having a transition metal layer for gas detection, is closely similar and matched to first sensing element 10 and is preferably manufactured from the same chip as first sensing element 10 so as to exhibit closely matched characteristics thereto, particularly as regards the absorption edge wavelength. Sensing elements 10 and 18 are preferably mounted in close proximity to one another or otherwise thermally coupled for temperature equalization. Sensing element 18 is enclosed in a sealed enclosure 26.

Electromagnetic radiation, such as an infrared beam 20 is transmitted through sensing element 18 and the resulting transmitted beam 22 is applied to a detector 24 which is essentially similar to detector 16. Detector 24 is preferably enclosed within sealed enclosure 26, though this is not essential, as indicated by the dashed line 28. Sensing element 18 and detector 24 are designated together as a sealed sensor 25.

The electrical outputs of detectors 16 and 24 are respectively applied to inputs of a computer 30. An output of computer 30, marked CONTROL in FIG. 1 is applied to the tuning control input of a tunable laser 32. The optical output of laser 32 is applied to a beam splitter 34 which produces two outputs, previously referred to as infrared beams 12 and 20 and which are the input beams to sensing elements 10 and 18, respectively. The output of active sensor 17 is optionally also applied to an output device 36.

In FIG. 1, dashed line 38 indicates a package boundary enclosing the complete compensated opto-electronic gas detector system.

Furthermore, computer 30 is arranged to be able to control the Wavelength $\lambda$ from $\lambda_1$ through $\lambda_2$ such that $\lambda_1 \geq \lambda \geq \lambda_2$ where $\lambda_1$, is in a region where the sensing element is always transparent; and where $\lambda_2$ is in a region where the sensing device is always opaque.

This means that the wavelength sweep or frequency scan is arranged to straddle the range within which the absorption edge is known to lie. Reference is made to FIG. 2.

In operation, $\lambda$ is swept from $\lambda_1$ to $\lambda_2$. Computer 30 monitors the output of detector 24 and thereby ascertains the characteristics of sensing element 18. Because sensing element 18 is sealed away from any gas to be sensed, the sensed characteristics correspond to "no gas sensed" and to the prevailing physical conditions, such as the prevailing ambient temperature. The sensed characteristics also closely correspond to the characteristics of active sensor element 10 under the same prevailing conditions, including ageing, because sensor elements 10 and 18 are closely matched, as was explained. These characteristics are stored as part of a calibration cycle.

It is not essential that a calibration step be performed in this manner. Feedback control can be utilized to set the wavelength at a particular value which causes and maintains a particular output of detector 24 known to correspond to proper location of the wavelength relative to the absorption band edge.

Thereafter, computer 30 is arranged to tune laser 32 to a wavelength optimally in the transition region where the sensitivity to a gas-induced shift in the absorption edge wavelength is highs. The optimum is determined from a knowledge of the slope in the rate of change of transmission as a function of wavelength.

Accordingly, calibration of active sensor 17 has been achieved for the particular device and for the prevailing ambient temperature. Calibration can be on a continuous or periodic basis. Because the computer monitors the output of sealed sensor 25, the laser tuning compensates for any sensor drift which is due to temperature or ageing and the like, but which is not due to the presence of a gas. Upon the detection of a change due to the presence of a gas, active sensor 17 will provide an output indication to output device 36 and to computer 30 which may thereupon, for example, provide a signal to a control device (not shown) for controlling parameters in a system responsive to the detection of a predetermined level of a gas.

The sealed sensor has been referred to herein, including in the claims, as a sensor for sensing gas. However, it is understood that the second sensing element 18 is not actually exposed to the gas to be sensed and will not be required to actually perform a sensing function. Accordingly, it need not be complete in all respects to fulfill the function assigned to it for calibration. In practice it is more convenient to simply use a second sensor from the same wafer as the active sensor so that they will in effect be identical. However, the distinction should be borne in mind.

While the invention has been described by way of exemplary embodiments, it will be understood by one of skill in the art that various changes and modifications may made without departing from the spirit of the invention. For example, the tunable laser beams may be coupled by direct radiation of a beam through space or coupling may be carried out by using fiber optic cable. Direct one-way transmission may be employed or a reflector may be used for a catoptrical system on the lines disclosed in the aforementioned U.S. Pat. No. 5,107,316. Furthermore, the laser source, with or without the computer, may be remotely located from the sensors. also, instead of using output device 36, computer 30 can develop a difference signal between the outputs of the detectors for providing a digital or a digitized quantitatively representative output signal. These and the like changes are understood to be within the scope of the claims following.

What is claimed is:

1. A compensated opto-electronic gas sensor system, comprising:
    a first opto-electronic gas sensor adapted for exposure to a gas to be detected;
    a second opto-electronic gas sensor, said second opto-electronic gas sensor being sealed against exposure to said gas and exhibiting closely matched characteristics to said first opto-electronic gas sensor;
    a wavelength tunable means for providing electromagnetic wave energy to said first and second gas sensors for the operation thereof;
    computer means coupled at least to said second opto-electronic gas sensors for sensing the respective output thereof and further coupled to said wavelength tunable means for controlling the wavelength of said electromagnetic wave energy.

2. A compensated opto-electronic gas sensor system as recited in claim 1, wherein said wavelength tunable means for providing electromagnetic wave energy to said first and second gas sensors comprises a tunable laser and means for splitting a beam of said electromagnetic wave energy.

3. A compensated opto-electronic gas sensor system as recited in claim 1, wherein said gas sensors comprise respective first and second quantum well structures having a transition metal layer for gas detection and exhibiting respective absorption wavelength edges for electromagnetic wave radiation at respective absorption wavelengths thereof.

4. A compensated opto-electronic gas sensor system as recited in claim 3, wherein said computer means controls said wavelength such that said wavelength is positioned in predetermined relationship to said absorption wavelength edge of said second quantum well structure.

5. A compensated opto-electronic gas sensor system as recited in claim 4, wherein said computer controls said wavelength by first sweeping through said absorption wavelength edge of said second quantum well structure so as to determine said absorption wavelength edge for said second quantum well structure by monitoring said respective output of said second gas sensor.

6. A compensated opto-electronic gas sensor system as recited in claim 5, wherein said computer controls said wavelength for sweeping through said absorption wavelength of said second quantum well structure by scanning between regions known to straddle said absorption wavelength edge of said second quantum well structure.

7. A compensated opto-electronic gas sensor system as recited in claim 6, wherein said computer stores a wavelength corresponding to said absorption wavelength edge of said second quantum well structure and controls said wavelength of said electromagnetic wave energy to be in said predetermined relationship to said absorption wavelength edge of said second quantum well structure.

8. A compensated opto-electronic gas sensor system as recited in claim 7, wherein said predetermined relationship to said absorption wavelength edge of said second quantum well structure is selected so as to provide an optimal response of said output of said first opto-electronic gas sensor for sensing gas.

9. A compensated opto-electronic gas sensor system as recited in claim 8, wherein said predetermined relationship to said absorption wavelength edge of said second quantum well structure is selected so as to provide said optimal response with regard to the slope of the rate of change of said output of said first opto-electronic gas sensor for sensing gas as a function of the wavelength of said electromagnetic wave energy.

10. A compensated opto-electronic gas sensor system as recited in claim 9, wherein said computer means is coupled to said first opto-electronic gas sensors for sensing the respective output thereof.

11. A compensated opto-electronic gas sensor system comprising:
    an active sensing element and a first detector for detecting an output of said active sensing element;
    a sealed sensing element and a second detector for detecting an output of said sealed sensing element and exhibiting characteristics closely matched to those of said active sensing element;
    said sensing elements comprising opto-electronic sensing elements of the type exhibiting respective quantum well structures having a transition metal layer for gas detection and exhibiting a respective absorption wavelength edge for electromagnetic wave radiation;
    a tunable wavelength source of electromagnetic wave radiation coupled providing electromagnetic wave radiation of the same wavelength to each of said active sensing element and said sealed sensing element; and
    computer means coupled to said first and second detectors and to a control input of said tunable wavelength source of electromagnetic wave radiation for controlling the wavelength of said electromagnetic radiation such that said wavelength is in predetermined relationship to said respective absorption wavelength edge of said sealed sensing element.

12. A compensated opto-electronic gas sensor system as recited in claim 11, wherein said predetermined relationship to said respective absorption wavelength edge of said sealed sensing element is preselected for optimal sensitivity of said active sensing element.

13. A compensated opto-electronic gas sensor system as recited in claim 12, wherein said computer means controls the wavelength of said electromagnetic radiation responsive to an output signal from said second detector.

14. A compensated opto-electronic gas sensor system as recited in claim 13, wherein said computer means continuously controls the wavelength of said electromagnetic radiation responsive to said output signal from said second detector.

15. A compensated opto-electronic gas sensor system as recited in claim 13, wherein said computer means periodically controls the wavelength of said electromagnetic radiation responsive to said output signal from said second detector.

16. A compensated opto-electronic gas sensor system as recited in claim 15, wherein said computer periodically determines said respective absorption wavelength edge of said sealed sensing element by controlling said wavelength so as to sweep over a band that straddles said respective absorption wavelength edge of said sealed sensing element while monitoring an output signal from said second detector.

17. A compensated opto-electronic gas sensor system comprising:
    active means utilizing electromagnetic radiation for sensing gas;
    sealed means utilizing electromagnetic radiation for sensing gas, said sealed means exhibiting matched characteristics to said active means;
    said means for sensing exhibiting a sensing sensitivity dependent upon the wavelength of said electromagnetic radiation;
    tunable wavelength means respectively coupled to said means for sensing gas for supplying electromagnetic radiation of a selectable wavelength thereto; and computer means respectively coupled to at least said sealed means for sensing gas and being responsive to an output thereof for controlling the wavelength of said electromagnetic radiation such that said sealed means for sensing gas exhibits an optimal sensitivity.

18. A compensated system for opto-electronically sensing a gas, comprising:

means for transmitting electromagnetic radiation of a given wavelength through a first quantum well structure exhibiting a first absorption band edge, having a thin mesh of a transition metal formed thereon, and being exposed to said gas;

means for transmitting electromagnetic radiation of said given wavelength through a second quantum well structure exhibiting a second absorption band edge, having a thin mesh of a transition metal formed thereon and being shielded from said gas, said first and second quantum well structures exhibiting closely matched characteristics;

means for monitoring electromagnetic radiation transmitted through said second quantum well structure;

means for adjustably providing said electromagnetic radiation at a given wavelength until it is in predetermined relationship with said second absorption band edge; and means for monitoring electromagnetic radiation transmitted through said first quantum well structure for detecting said gas.

19. A compensated system for opto-electronically sensing a gas as recited in claim 18, wherein said means for adjustably providing said electromagnetic radiation at a given wavelength continuously adjusts said wavelength so as to maintain it in said predetermined relationship with said second absorption band edge.

20. A compensated system for opto-electronically sensing a gas as recited in claim 19, wherein said means for adjustably providing said electromagnetic radiation at a given wavelength periodically readjusts said wavelength so as to maintain it in said predetermined relationship with said second absorption band edge.

21. A compensated system for opto-electronically sensing a gas as recited in claim 20, wherein said means for adjustably providing said electromagnetic radiation at a given wavelength sweeps said wavelength while monitoring electromagnetic radiation transmitted through said second quantum well structure so as to determine said second absorption band edge.

22. A compensated method for opto-electronically sensing a gas, said method comprising the steps of:

transmitting electromagnetic radiation of a given wavelength through a first quantum well structure exhibiting a first absorption band edge, having a thin mesh of a transition metal formed thereon, and being exposed to said gas;

transmitting electromagnetic radiation of said given wavelength through a second quantum well structure exhibiting a second absorption band edge, having a thin mesh of a transition metal formed thereon and being shielded from said gas, said first and second quantum well structures exhibiting closely matched characteristics;

monitoring electromagnetic radiation transmitted through said second quantum well structure;

adjusting said given wavelength until it is in predetermined relationship with said second absorption band edge; and monitoring electromagnetic radiation transmitted through said first quantum well structure for detecting said gas.

23. A compensated method for opto-electronically sensing a gas as recited in claim 22, wherein said step of adjusting said given wavelength until it is in predetermined relationship with said second absorption band edge is performed continuously.

24. A compensated method for opto-electronically sensing a gas as recited in claim 23, wherein said step of adjusting said given wavelength until it is in predetermined relationship with said second absorption band edge is performed periodically.

25. A compensated method for opto-electronically sensing a gas as recited in claim 24, wherein said step of adjusting said given wavelength until it is in predetermined relationship with said second absorption band edge includes a step of sweeping said wavelength while monitoring electromagnetic radiation transmitted through said second quantum well structure so as to determine said second absorption band edge.

* * * * *